US 6,800,066 B2

(12) United States Patent
Targell

(10) Patent No.: US 6,800,066 B2
(45) Date of Patent: Oct. 5, 2004

(54) RETRACTABLE NEEDLE SYRINGE

(75) Inventor: John Targell, Ayrshire (GB)

(73) Assignee: NMT Group PLC, Livingston (GB)

(*) Notice: Subject to any disclaimer, the term of this patent is extended or adjusted under 35 U.S.C. 154(b) by 0 days.

(21) Appl. No.: 10/133,104

(22) Filed: Apr. 26, 2002

(65) Prior Publication Data
US 2002/0183699 A1 Dec. 5, 2002

Related U.S. Application Data
(60) Provisional application No. 60/290,733, filed on May 14, 2001.

(30) Foreign Application Priority Data
Apr. 26, 2001 (GB) .............................................. 0110194

(51) Int. Cl.[7] .............................................. A61M 5/00
(52) U.S. Cl. ..................................................... 604/110
(58) Field of Search ................................ 604/110, 195, 604/192, 198, 187, 263

(56) References Cited

U.S. PATENT DOCUMENTS

| | | | |
|---|---|---|---|
| 4,446,984 A | 5/1984 | Roth et al. | |
| 4,460,534 A | 7/1984 | Boehm et al. | |
| 4,973,316 A | 11/1990 | Dysarz | |
| 4,978,343 A | 12/1990 | Dysarz et al. | |
| 4,994,034 A | 2/1991 | Botich et al. | |
| 5,000,736 A | 3/1991 | Kaufhold, Jr. et al. | |
| 5,019,044 A | 5/1991 | Tsao | |
| 5,084,018 A | 1/1992 | Tsao | |
| 5,114,410 A | 5/1992 | Caralt Batlle | |
| 5,125,898 A | 6/1992 | Kaufhold, Jr. et al. | |
| 5,180,369 A | 1/1993 | Dysarz | |
| 5,180,370 A | 1/1993 | Gillespie | |
| 5,188,599 A | 2/1993 | Botich et al. | |
| 5,385,551 A | 1/1995 | Shaw | |
| 5,407,431 A | 4/1995 | Botich et al. | |
| 5,407,436 A | 4/1995 | Toft et al. | |

(List continued on next page.)

FOREIGN PATENT DOCUMENTS

| | | |
|---|---|---|
| EP | 0300694 A1 | 1/1989 |
| EP | 0413414 A1 | 2/1991 |
| EP | 0747075 A2 | 12/1996 |
| EP | 0753323 A1 | 1/1997 |
| EP | 0 776 225 B1 | 3/1998 |
| EP | 0895848 A1 | 2/1999 |
| EP | 0911132 A2 | 4/1999 |
| FR | 2755614 | 5/1998 |
| NZ | 231563 | 11/1991 |
| WO | WO98/13077 | 4/1998 |
| WO | WO98/48869 | 11/1998 |
| WO | WO 01/42104 A1 | 6/2001 |
| WO | WO 01/62320 A1 | 8/2001 |
| WO | WO 01/62320 | 8/2001 |

Primary Examiner—Sharon Kennedy
(74) Attorney, Agent, or Firm—Baker & Daniels

(57) ABSTRACT

A fluid handling device comprises a barrel for containing fluid to be delivered through a needle, a needle-mounting hub at one end of the barrel, a biasing element arranged to urge the hub inwardly of the barrel, a stop element blocking inward movement of the hub into the barrel, and a hollow plunger which is movable within the barrel to deliver fluid from the barrel via the needle and has at its forward end a portion which is severable in response to movement of the plunger over the final part of, or at the conclusion of, its delivery stroke to allow retraction of the needle-mounting hub into the hollow plunger, the hub and the stop element being formed as plastics mouldings in such a way that the stop element is axially captive with the hub and the plunger being arranged to disengage the stop element and the hub during said final part of, or at the conclusion of, the delivery stroke to allow the biasing element to drive the needle into the hollow plunger.

21 Claims, 2 Drawing Sheets

U.S. PATENT DOCUMENTS

| | | | |
|---|---|---|---|
| 5,578,011 A | 11/1996 | Shaw | |
| 5,613,952 A | 3/1997 | Pressly, Sr. et al. | |
| 5,632,733 A | 5/1997 | Shaw | |
| 5,769,822 A | 6/1998 | McGary et al. | |
| 5,800,403 A | 9/1998 | Pressly, Sr. et al. | |
| 5,902,276 A | 5/1999 | Namey, Jr. | |
| 5,935,104 A | * 8/1999 | Janek et al. | 604/110 |
| 5,997,512 A | 12/1999 | Shaw | |
| 6,010,486 A | 1/2000 | Carter et al. | |
| 6,015,438 A | 1/2000 | Shaw | |
| 6,074,370 A | 6/2000 | Pressly, Sr. et al. | |
| 6,090,077 A | 7/2000 | Shaw | |
| 6,099,500 A | * 8/2000 | Dysarz | 604/110 |
| 6,123,688 A | 9/2000 | Botich et al. | |
| 6,139,305 A | 10/2000 | Nesch | |
| 6,179,812 B1 | 1/2001 | Botich et al. | |
| 6,368,303 B1 | 4/2002 | Caizza | |

* cited by examiner

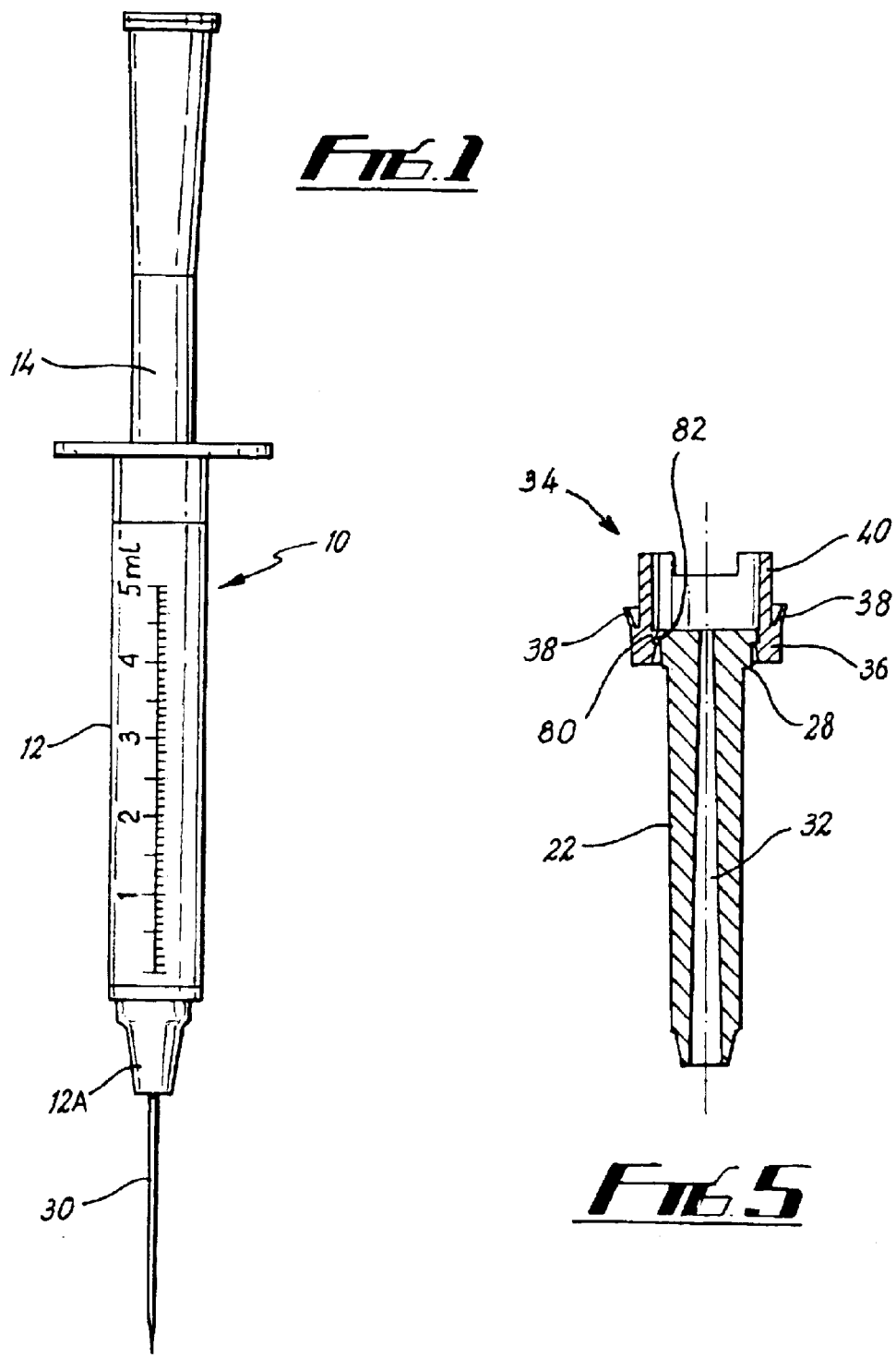

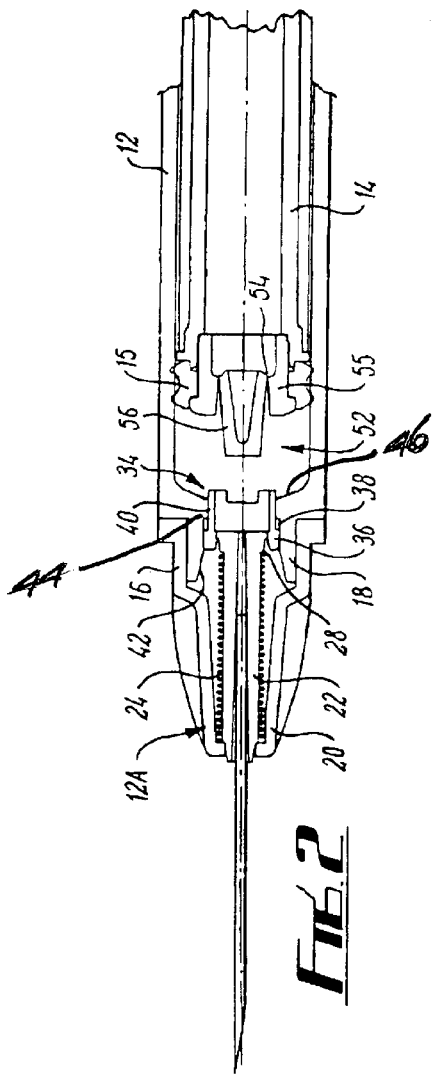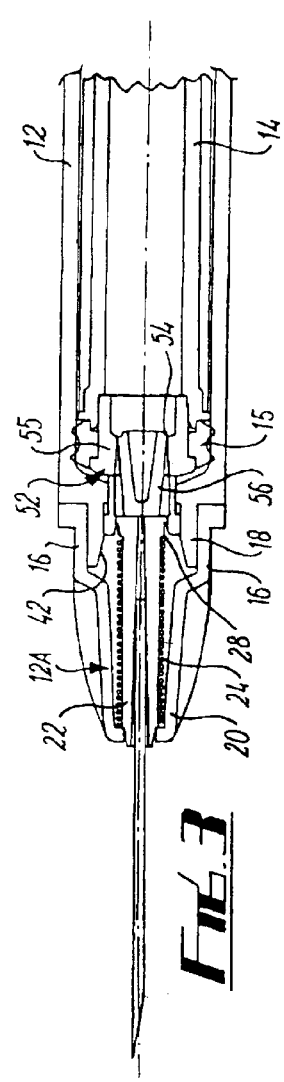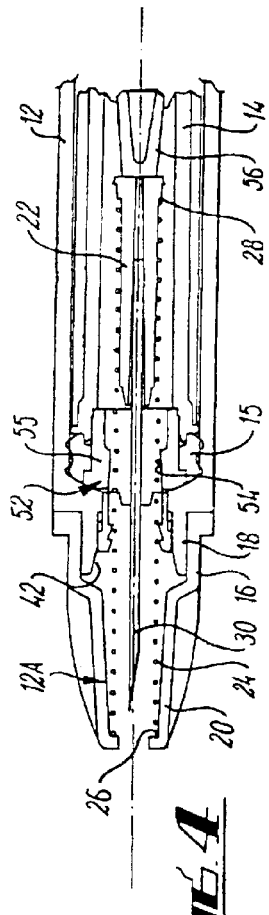

RETRACTABLE NEEDLE SYRINGE

This application claims benefit of No. 60/290,733 filed May 14, 2001.

BACKGROUND OF THE INVENTION

This invention relates to fluid handling devices, such as medical syringes, in which a plunger is used to deliver fluid from a barrel of the device via a needle.

For safety reasons, e.g. to avoid needle stick injuries, it is desirable that the needle is retracted into the barrel following delivery of the fluid. Our prior U.S. Pat. No. 5,782,804 discloses a fluid handling device provided with a needle retraction mechanism of this type.

The present invention seeks to provide a fluid handling device having a simplified needle retraction mechanism.

SUMMARY OF THE INVENTION

According to the present invention there is provided a fluid handling device comprising a barrel for containing fluid to be delivered through a needle, a needlemounting hub at one end of the barrel, a biasing element arranged to urge the hub inwardly of the barrel, a stop element blocking inward movement of the hub into the barrel, a hollow plunger which is movable within the barrel to deliver fluid from the barrel via the needle and has at its forward end a portion which is severable in response to movement of the plunger over the final part of, or at the conclusion of, its delivery stroke to allow retraction of the needlemounting hub into the hollow plunger, the hub and the stop element being formed as plastics mouldings in such a way that the stop element is axially captive with the hub and the plunger being arranged to disengage the stop element and the hub during said final part of, or at the conclusion of, the delivery stroke to allow the biasing element to drive the needle into the hollow plunger.

The stop element may incorporate an integral seal, e.g. a lip seal, which may be annular so as to encircle the stop element.

The stop element and the hub may have interengaged formations at the location of the moulding interface which are caused to separate from one another during said final part of, or at the conclusion of, the delivery stroke of the plunger.

The stop element and the hub may alternatively or additionally be at least partially united. e.g. partially fused, together at the moulding interface, the arrangement being such that the connection is fractured or broken during said final part of, or at the conclusion of, the delivery stroke.

The hub may be elongate and may have a central bore for reception of the needle.

The needle-receiving bore may be of reducing cross-section.

The hub may be produced with some degree of draft, i.e. so as to be of reducing cross section in a direction of travel of the plunger during its delivery stroke.

The biasing element may be a helical spring, usually a compression spring, which may be arranged in encircling relation with the hub. One end of the spring may coact with a forward end of the barrel or an end cap attached to the main body of the barrel and the opposite end of the spring may coact with the hub at a location inwardly of the forward end of the barrel.

The forward end of the plunger may comprise a rim portion and a central blocking portion, the latter forming said severable portion.

The arrangement may be such that, during the final part of or at the conclusion of the plunger delivery stroke, the rim portion of the plunger is arranged to engage the stop element while the hub is arranged to engage the blocking portion, the engagement between the two sets of components being effective to free the hub from the stop element and to free the blocking portion from the rim portion at least to the extent necessary to allow the hub to enter the interior of the plunger.

Preferably the hub is freed from the stop element before the blocking portion is at least partially freed from the rim portion; however, if desired the blocking portion may be freed first or alternatively the hub and the blocking portion may be freed substantially. simultaneously.

The arrangement may be such that the hub and stop element are united together by the moulding process to afford a well-defined threshold at which they break away from one another in response to the application of force to the stop element in the course of operating the plunger.

Preferably one of the components (hub and stop element) is produced as a plastics moulding in a mould having moulding surfaces defined, in part, by the other component, i.e. moulding of one component being effected with the other component in situ.

The two portions may be of plastics materials having different chemical compositions and/or characteristics or they may both be of substantially the same or a similar plastics material.

The hub and stop element may be capable of being broken away from each other without deformation of either of the two portions and, to this end, the moulding interface may be shaped so that no deformation of either component occurs when breaking one from the other.

Alternatively, the hub and the stop element may be interlocked with each other so that some deformation of at least one of the parts occurs when effecting the break.

At the moulding interface, an annular surface of one of the components may be have a configuration complementary with an annular surface of the other component.

The annular surfaces may be cylindrical or of other configuration, e.g. conical.

At the moulding interface, the components may intimately contact each other with a degree of fusion bonding consistent with securing fracture preferentially at the interface region during the break.

The assembly of the hub and stop element may include a detent arrangement acting between the components. The detent arrangement may be provided at or in the vicinity of said moulding interface. For example, the hub and the stop element may, by virtue of the mould design, have interengaging formations which lock the components together to prevent separation, and at least one of the formations may be resiliently deformable to allow the disengagement of the formations on application of sufficient loading to the stop element relative to the hub.

Resistance to separation of the two components may additionally or alternatively be afforded by the nature of the interaction between material or materials of the hub and the stop element at the moulding interface. For instance, there may a shrink type fit between the components at the moulding interface obtained by material shrinkage during cooling following the moulding process.

As a further addition or alternative to the detent arrangement and/or shrink type fit mentioned above, resistance to separation may be provided by fusion bonding between the components at the moulding interface. Such fusion bonding may range from relatively weak, e.g. as a result of some degree of diffusion of material from one component across the moulding interface into the other component, through to relatively strong.

Depending on the nature of interaction desired between the hub and the stop element at the moulding interface, the material or materials from which said portions are produced may be selected so as to secure the desired extent of fusion bonding, if any. For example, if negligible fusion bonding is desired, the materials employed will usually differ in chemical and/or physical characteristics and will be such that no significant diffusion of material takes place across the moulding interface as a result of the moulding process. Similarly the materials can be appropriately selected to obtain the desired degree of fusion bonding where there is a requirement to develop a fusion bond at the moulding interface.

In the latter case for example, the hub and the stop element may be composed of the same material so that significant fusion of the material takes place between the two components.

The width of the moulding interface and hence the zone of contact between the two components may be selected with regard to the required effectiveness of the seal and/or with regard to the resistance to separation of the components required at said interface. For instance, a given degree of resistance may be secured by a relatively narrow interface where the components are strongly fusion bonded together whereas a wider interface may be required if resistance is afforded by shrinkage and/or a weak fusion bond.

Irrespective of how the hub and the stop element are coupled together, the arrangement may be such that the resistance to separation of the two parts is greater with respect to forces applied in one direction compared with forces applied in the opposite direction.

Where one part is moulded in advance of the other and the second part is then moulded with the first part in situ, the first part to be moulded may have a higher heat distortion temperature than the second part so that the first part is not deformed during moulding of the second part.

The stop element and the hub may advantageously be formed in a two-shot moulding process in which one component, e.g. the hub, is initially formed and located so that an annular surface thereof forms a boundary surface of the mould cavity in which the other component is produced so that, during formation of the second component, an annular surface of the latter is conformed with the annular surface of the first component.

The manner of coupling together the hub and the stop element as referred to in the preceding paragraphs may also be employed to couple together the rim portion and the blocking portion, e.g. as disclosed in our U.S. patent application Ser. No. 10/149,342, the entire disclosure of which is incorporated herein by this reference.

Other aspects of the invention include a needle-mounting hub assembly produced as a two-shot moulding and comprising a hub and a stop element captive with the hub, and a method of manufacturing such an assembly.

BRIEF DESCRIPTION OF THE DRAWINGS

The invention will now be described by way of example with reference to the accompanying drawings in which:

FIG. 1 is a side view of a syringe which may embody features of the present invention;

FIG. 2 is a fragmentary sectional view of the syringe showing the plunger approaching the final part of its delivery stroke;

FIG. 3 is a similar view to that of FIG. 2 but with the plunger shown at its point of initial contact with the crown associated with the needlemounting hub;

FIG. 4 is similar view to that of FIG. 2 at the conclusion of the plunger delivery stroke and showing the needle undergoing retraction into the hollow plunger; and FIG. 5 is detail view of the needle-mounting hub and crown.

DETAILED DESCRIPTION OF THE INVENTION

Referring now to the drawings, the disposable medical syringe 10 comprises a hollow barrel 12, from the rear of which (upper end as viewed in FIG. 1) protrudes a plunger 14. A seal 15 is mounted on the plunger to ensure a fluid tight seal with the internal wall of the barrel. The barrel 12 includes an end cap 12A including a cylindrical section 16 which is engaged with a annular collar 18 of the main body of the barrel 12 and a generally conical section 20. The end cap 12A may be permanently bonded to the main body of the barrel 12 or it may be releasably attached thereto. A needle-mounting hub 22 is accommodated within the end cap 12A and is encircled by a spring 24 which engages at its forward end with a flange 26 of the conical section 20 and at its rear end with a radial shoulder 28 on the hub 22 and serves to bias the hub 22 and needle 30 inwardly relative to the barrel 12.

The hub 22 is of generally cylindrical configuration and has an axial bore 32 for reception of the needle 30. The bore 32 may be a throughbore as illustrated. The bore 32 is of tapering configuration to allow the needle to be fitted to the hub as a press-fit or by spin-welding either before or after the end cap 12A has been assembled to the main body of the barrel.

Rearward movement of the hub and needle assembly is prevented by a stop element in the form of a crown 34 which is carried by hub 22 and is received within the annular collar 18. The crown 34 is of generally cylindrical configuration and comprises a forward portion 36 incorporating an integral annular lip seal 38 and a reduced diameter portion 40. As shown in FIG. 5, prior to insertion into the annular collar 18, the lip seal flares outwardly as shown in FIG. 5 and is resiliently flexible so that, on insertion into the collar, it is deflected radially inwardly so as to bear against and make sealing engagement with the inner surface of the collar 18. At its forward end, the collar 18 includes a lead-in portion 42 to facilitate insertion of the crown 34.

The hub and crown are produced as plastics mouldings by two-shot moulding which serves to integrate the two components and render them captive with each other so that they effectively constitute a one-piece component designed to fracture at the interface between the hub and the crown when subjected to a predetermined forwardly directed axial force. In addition, the assembly of hub and crown incorporates the lip seal 38 which may be integral with the crown since the latter can be moulded from polyethylene for example. In this way, needle mounting and sealing at the forward end of the barrel is considerably simplified compared for example with the arrangement disclosed in our prior U.S. Pat. No. 5,782,804. At the interface between the hub and crown, the components may have interfitting formations, e.g. mating frusto-conical surfaces, which may determine at least in part the force needed to separate the two components.

The plunger 14 is hollow and has a closed trailing end. The forward end of the plunger is arranged to receive a closure assembly comprising an insert 52 which engages firmly in the plunger to form an end wall of the plunger while defining an aperture 54 which is sufficiently large to allow the needle 30 and hub 22 to pass through during needle retraction.

The insert 52 comprises a rim portion 55 fitted with a forwardly projecting blocking portion 56 of generally frusto-conical configuration so that the blocking portion 56 closes and seals the aperture 54. The blocking portion 56 and rim portion 55 seal the forward end of the plunger to prevent ingress of liquid into the plunger interior from the interior of barrel 12.

The rim and blocking portions 55, 56 are also formed as plastics mouldings by two-shot moulding so that the two portions 55 and 56 are integrated and captive with each other. A closure assembly of this form is disclosed in U.S. patent application Ser. No. 10/149,342 (the entire contents of which are incorporated herein by this reference) and the design of these components may be as described and illustrated therein. The rim and blocking portions 55, 56 are coupled together in such a way that they can be separated from each other in response to the application of a predetermined axial force as described in U.S. patent application Ser. No. 10/149,342.

Although the hub 22 and crown 34 may have interengaging formations 80, 82 at the interface between them such that these formations render the respective components captive to one another and contribute to the resistance to separation of the components, such interengaging formations 80, 82 are not essential as long as sufficient resistance to separation at the interface is available, e.g. as described below. Whether or not such formations are provided, it will be appreciated that the "forceto-break" or allow the components to separate from each other can be tailored according to requirements by appropriate design of features such as the angle of the interface between the two parts and/or the surface texture present at the interface and/or extent of the interface.

In accordance with a preferred feature of the invention, each assembly comprising parts 22, 34 and 55, 56 respectively is produced by a two-shot moulding process, for instance a first stage in which the inner part 22, 56 is produced followed by a second stage in which the outer part 34, 55 is moulded onto the inner part 22, 56 thereby connecting the two parts together, e.g. through the interengaging formations 80, 82 (if present) and/or through a zone of intimate contact which sealingly engages the two parts with each other at the moulding interface. Two-shot moulding technology may be carried out for instance using a multi-stack moulding machine such as available from Milacron Inc of Cincinnati, Ohio, USA in which a two-sided pivoting centre platen allows two simultaneous moulding operations to be carried out. The process starts with a preform injected into cavities on one mould face. The mold opens, the centre platen swivels through 180 degrees in a vertical plane, locks into position, the mold closes, and a second material component is injected. At the same time, another pre-form is injected into the opposite mould face of the centre platen. In this way, a preform and a completed part are injection-moulded simultaneously during each cycle of operation using two plastic melts which may be the same material, similar or different materials. A two-shot moulding machine is also disclosed in U.S. Pat. No. 6,139,305.

To prevent the inner and outer parts 22, 34 and 55, 56 welding together inseparably during the moulding process, the two parts may be moulded using materials which are compatible with each other and have different characteristics. However, some degree of fusion bonding between the rim and closure parts may be desirable, e.g. to ensure sealing and, where desired, to play a role in predetermining the loading necessary to break the blocking portion away from the rim portion.

The closure assembly in FIGS. 2 to 4 is shown fitted into the forward end of the plunger 6; however, in an alternative embodiment, the rim portion may be formed integrally with at least the forward end portion of the plunger so that the plunger and rim portion can be produced as a single moulding. For example, both the plunger and rim portion may be made from a plastics material such as polyethylene or polypropylene. In this case, the other end of the plunger may be closed by an end cap.

The parts 22, 34 and 55, 56 may be held captive to one another by interengaging formations 80, 82 (as illustrated for parts 22, 34) which may act as a detent-type arrangement. However, instead of or in addition to such a detent-type arrangement, the parts may be rendered captive to one another as a result of some degree of fusion or bonding of the materials at the interface and/or by virtue of an interference or shrink type fit between the parts at a zone of contact, e.g. as illustrated in FIG. 3 of U.S. patent application Ser. No. 10/149,342. The shrink fit may be obtained during the moulding process by moulding the outer part 34, 55 around the inner part 22, 56 and exploiting material shrinkage on cooling to secure the interference fit. Where the inner part is held captive in this way, there is not necessarily any significant fusion bonding between the materials although, if desired, the material(s) may be selected so that such fusion bonding is present, e.g. as a result of some degree of diffusion of material between the two parts.

When the hub and crown are assembled as shown in FIG. 2, the rearward end of the lip seal 38 engages a shoulder 44 while the reduced diameter portion 40 of the crown projects beyond an annular end wall 46 of the main body of the barrel 12 for cooperation with the forward end of the plunger 14 as described below. Likewise, the blocking portion 56 is arranged for entry into the opening defined by the crown 34 to contact the rearward end of the hub 22.

In operation, as the plunger 14 is displaced inwardly into the barrel 12, the contents of the barrel are delivered through the needle. As the plunger approaches completion of its stroke, the condition shown in FIG. 3 is reached in which the rim portion 55 is in contact with, or about to contact, the rearward end of the crown 34 while the blocking portion 56 is in contact with, or about to contact, the rearward end of the hub 22. By appropriate design of the components, the axial force developed by continued displacement of the plunger to the completion of its stroke (see FIG. 4) results in the connections between the parts 22, 34 and 55, 56 being broken, e.g. fractured, freeing the hub 22 from the crown 34 and freeing of the blocking portion 56 from the rim portion 55.

More specifically, the rim portion 55 displaces the crown 34 forwardly while engagement between the hub, which is blocked from forward movement by the forward end of the portion 12A, and the blocking portion 56 exerts a rearwardly directed force on the latter. Under these conditions, once the connections rendering parts 22, 34 and 55, 56 captive with one another are broken, the spring 24 is no longer restrained and becomes effective to propel the hub through the crown, through the aperture created by freeing of the blocking portion 56 and into the interior of the plunger thereby concealing the needle and avoiding the risk of needle stick injury once the contents of the syringe have been delivered. Freeing of the hub and the blocking portion may occur substantially simultaneously or in sequence, freeing of the hub first being currently preferred. The forces required to effect freeing of the hub and the blocking portion may be readily tailored to requirements by for example appropriate selection of the dimensioning/configuration of the components, tuning of the two-shot moulding process etc.

In the course of being displaced by the rim portion 55, the extent of travel of the crown 34 is such that the lip seal 38 remains in sealing contact with the internal surface of the collar 18. Although the hub may be of generally cylindrical configuration, it is desirable to produce it with a draft (i.e. of reducing cross-section from its trailing end towards its forward end) so as to facilitate easy ejection and prevent binding of the spring against the peripheral surface of the hub. The hub may be manufactured so that, when assembled as shown in FIG. 2, there is a small clearance between the shoulder 28 and the adjacent end wall of the end cap 12A thereby eliminating any risk of the hub/crown hub connection being broken during assembly of the syringe (i.e. because of tolerance variations in the length of the hub). This clearance is taken up as when the rim portion of the plunger initially contacts and begins to displace the crown.

From the foregoing, it will be seen that the present invention as embodied in the illustrated syringe results in a much simplified design compared with that of U.S. Pat. No. 5,782,804. Advantages that can be realized include the following:

- better control of the release force needed to separate the hub from the crown since the two-shot moulding can be tuned to requirements;
- the possibility of increasing the diameter of the spring to allow a shorter, more robust design;
- an integral lip seal rather than an "0" ring seal which reduces the risk of premature firing and low pressure failures;
- a shorter travel of the crown with reduced risk of accidental firing when expelling air;
- reduced tolerance dependency;
- greater control of the timing/sequencing of the needle retraction process;
- simplified assembly since the hub/crown/lip seal effectively comprises a single component;
- redesign of the end cap 12A to enable easier moulding;
- possibility of needle insertion into the hub after the latter has been installed, thereby reducing the risk of needle damage;
- hub design permits press-fit or spin-weld needle fixation;
- ullage can be reduced and be more consistent; and
- higher locking force (inserting needle into vials etc) as the hub and crown are moulded in one piece.

While endeavoring in the foregoing specification to draw attention to those features of the invention believed to be of particular importance, it should be understood that the Applicant claims protection in respect of any patentable feature or combination of features disclosed herein and/or shown in the drawings whether or not particular emphasis has been placed on such feature or features.

What is claimed is:

1. A syringe device comprising:
   a barrel for containing fluid to be delivered through a needle;
   a needle mounting hub at one end of said barrel and a needle mounted in said hub;
   a biasing element operatively arranged to urge said hub inwardly into said barrel;
   a stop element adapted to block inward movement of said hub into said barrel;
   a hollow plunger which is movable within said barrel with a delivery stroke to deliver fluid from said barrel to said needle, said plunger adapted to allow retraction of said hub and needle into said plunger at the conclusion of the delivery stroke of the plunger, the forward end of the plunger comprising a rim portion and a central blocking portion, said central blocking portion separable from said rim portion;
   said hub and stop element comprising molded plastic components, said hub and stop element separably, sealingly, intimately, and form fittingly engaging one another along a substantially axial interface; and
   said hub and stop element adapted to disengage from one another along said interface at the conclusion of said plunger delivery stroke to allow said biasing element to drive said needle into said hollow plunger.

2. A device as claimed in claim 1 in which the stop element incorporates an integral seal which sealingly engages said barrel.

3. A device as claimed in claim 2 in which the seal comprises an annular lipseal which encircles the stop element.

4. A device as claimed in claim 1 in which the stop element and the hub each include a formation, said formations interengaging one another along said interface to define said form fit.

5. A device as claimed in claim 1 in which the stop element and the hub are adheringly connected to one another along at least a portion of said interface, whereby the connection between said hub and said stop element is broken at the conclusion of the plunger delivery stroke.

6. A device as claimed in claim 1 in which the hub is elongate and has a central bore for receiving said needle.

7. A device as claimed in claim 6 in which the needle-receiving bore is of reducing cross-section.

8. A device as claimed in claim 1 in which the hub includes some degree of draft so as to be of reducing cross section in the direction of travel of the plunger during its delivery stroke.

9. A device as claimed in claim 1 in which the biasing element is a helical spring encircling one of said hub and said needle.

10. A device as claimed in claim 1 in which the arrangement is such that, at the conclusion of the plunger delivery stroke, the rim portion of the plunger is adapted to engage the stop element while the hub is adapted to engage the blocking portion, such engagement adapted to separate the hub from the stop element and to separate the blocking portion from the rim portion to thereby permit the hub to enter the hollow plunger.

11. A device as claimed in claim 1 in which the hub is separated from the stop element before the blocking portion is at least partially separated from the rim portion.

12. A device as claimed in claim 1 in which the blocking portion is separated before the stop element separates.

13. A device as claimed in claim 1 in which the hub and the blocking portion are separated substantially simultaneously.

14. A device as claimed in claim 1 in which the hub and stop element are made of different plastic materials having different characteristics.

15. A device as claimed in claim 1 in which the hub and stop element are made of substantially similar plastics material.

16. A device as claimed in claim 1 in which the hub and stop element are adapted to separate from one another substantially without deformation of either of the hub or stop element.

17. A device as claimed in claim 1 in which the hub and stop element are interlocked with one another so that some deformation of at least one of the hub and stop element occurs when the hub and stop element separate from one another.

18. A device as claimed in claim 1 in which the hub and stop element each include an annular surface, said annular surfaces complementary with one another to define said interface.

19. A device as claimed in claim 18 in which said annular surfaces are one of a substantially cylindrical and conical configuration.

20. A device as claimed in claim 1 in which the hub and stop element intimately contact one another at said interface with a degree of fusion bonding.

21. A device as claimed in claim 1 in which the hub and stop element engage one another with a detent arrangement along said interface.

* * * * *